United States Patent
Pesu et al.

(10) Patent No.: US 7,277,626 B2
(45) Date of Patent: Oct. 2, 2007

(54) ILLUMINATED AIR FRESHENER

(75) Inventors: Bradley Pesu, Gahanna, OH (US); Cheriyan Thomas, New Albany, OH (US)

(73) Assignee: Bath & Body Works Brand Management, Inc., Reynoldsburg, OH (US)

( * ) Notice: Subject to any disclaimer, the term of this patent is extended or adjusted under 35 U.S.C. 154(b) by 0 days.

(21) Appl. No.: 10/656,752

(22) Filed: Sep. 4, 2003

(65) Prior Publication Data
US 2005/0053368 A1    Mar. 10, 2005

(51) Int. Cl.
F24F 6/00 (2006.01)
F24F 6/08 (2006.01)

(52) U.S. Cl. .................... 392/390; 392/395

(58) Field of Classification Search ........ 392/386, 392/387, 390, 391, 392, 394, 395; 122/366; 239/34, 44, 45; 219/482, 483
See application file for complete search history.

(56) References Cited

U.S. PATENT DOCUMENTS

| | | | | |
|---|---|---|---|---|
| 3,373,341 A | * | 3/1968 | Wattson | 323/277 |
| 3,386,005 A | * | 5/1968 | Roland et al. | 361/59 |
| 4,968,487 A | * | 11/1990 | Yamamoto et al. | 422/125 |
| 5,175,791 A | * | 12/1992 | Muderlak et al. | 392/390 |
| 5,274,215 A | * | 12/1993 | Jackson | 219/439 |
| 5,716,119 A | * | 2/1998 | Patel | 362/551 |
| 6,044,202 A | * | 3/2000 | Junkel | 392/390 |
| 6,236,807 B1 | * | 5/2001 | Ruffolo et al. | 392/390 |
| 6,278,840 B1 | * | 8/2001 | Basaganas Millan | 392/390 |
| 6,627,857 B1 | * | 9/2003 | Tanner et al. | 219/445.1 |

* cited by examiner

Primary Examiner—Sang Paik
(74) Attorney, Agent, or Firm—Ward & Olivo

(57) ABSTRACT

Disclosed is a novel apparatus and method that combines a nightlight and an air freshener in a single device. The apparatus includes circuitry where a single resistor heats a heating block that heats and releases a volatile aromatic. The resistor also limits the current that passes through one or more light emitting diodes. The aromatic may be liquid scented oil held by a container. The container may also include a protruding wick that is heated by the heating block to facilitate oil evaporation. The light emitting diodes illuminate the housing and a decorative shield. The diodes may also illuminate fiber optic cables. The apparatus receives alternating current from a standard wall outlet. The circuitry utilized by the device ensures that the resistor is continuously powered during both half-cycles of the alternating current resulting in optimal heating of the aromatic.

54 Claims, 10 Drawing Sheets

ILLUMINATED AIR FRESHENER

TECHNICAL FIELD OF THE INVENTION

The present invention relates generally to a device that functions as both an air freshener and a nightlight. More specifically, the present invention relates to circuitry and structure that optimally combine nightlight and air freshening components. Thus, the present invention advances upon the ability to combine air fresheners and nightlights into a single device.

BACKGROUND OF THE INVENTION

Air fresheners have existed for quite some time. Generally, an air freshener is used to emit a pleasant aroma into a room or enclosed area. Often the aroma is used to mask unpleasant odors. Alternatively, the aroma released by an air freshener may be used to create a mood or invoke a psychological response. In some instances, aromas are used for therapeutic purposes.

One of the most common methods for implementing an air freshener is to use a heating element to motivate the evaporation of an aromatic or fragrant compound into the atmosphere. Usually, an air freshener is plugged into a standard wall outlet, which provides both power and physical support. The wall outlet supplies power in the form of alternating current ("AC") to the heating element, which in turn heats the fragrant compound. The heat causes the fragrant compound to evaporate, thereby emitting an aroma.

For example, one known device utilizes scented liquid held by a bottle. The bottle contains a wick that is submerged in the scented liquid at one end and protrudes from the bottle at the other end. The wick draws up the scented liquid by means of capillary action. The end of the wick protrudes from the bottle is located next to a heating element so that the drawn up scented liquid is evaporated by the heat emitted from the heating element. The evaporated liquid disperses into the atmosphere, thereby emitting an aroma.

Air fresheners may utilize a variety of heating elements. For example, some air fresheners utilize positive temperature coefficient (PTC) heating elements. Alternatively, a series of resistors may be used to heat the fragrant compound. It is also known to use resistors to heat a ceramic block, which in turn heats a wick saturated with a scented liquid. Using a power source (such as a standard wall outlet) in conjunction with one or more resistors has proven to be an effective way to emit an aroma.

Nightlights have also existed for some time. They are often used in a room or an enclosed area. Nightlights are used to assist in navigation and vision when it is desirable to forego the use of standard lights. For example, a resident of a house who may wake during the night can navigate a living area more expeditiously by using a nightlight. In doing so, he or she may be able to perform a variety of tasks without disturbing the other residents by turning on brighter lights. Additionally, like air fresheners, nightlights may be used to create a mood or invoke a psychological response. For example, a nightlight may be utilized in a child's room to allay a child's fear of the dark.

Also, like air fresheners, nightlights may be plugged into wall outlets for power and support. Specifically, the wall outlet is used to power the lighting element of the nightlight. For example, a nightlight may contain a circuit with a small incandescent bulb wired in series to a resistor and a pair of male terminals configured to be plugged into a standard 120 V, 60 Hz electrical socket. When this nightlight is plugged in, the bulb receives power from the wall outlet and illuminates.

The advantages of combining nightlight and air freshener capabilities are well-known. The applicant is aware of several devices that perform both of these functions.

Despite the existence of such devices, there is a clear need for a device that optimally combines air freshener and nightlight capabilities. The present invention improves upon existing devices and includes circuitry that optimally and efficiently combines air freshener and nightlight components. Additionally, the present invention includes configurations for optimal illumination and includes structures that enhance the decorative and illuminative effects of the nightlight components.

SUMMARY OF THE INVENTION

The present invention is a novel, optimized air freshener and nightlight. Specifically, the present invention provides an efficient circuitry design and a light configuration for optimal illumination. An apparatus of the present invention is preferably adapted to plug into an AC outlet, most preferably a 120 V, 60 Hz electrical outlet. The present invention may include a housing that holds the circuitry of the invention and is further configured to receive a container such as a bottle. The bottle and the housing preferably comprise a threaded male and female screw connector. The bottle of the present invention holds an aromatic, which is preferably a volatile scented liquid. A wick is inserted into the bottle and exposed to the atmosphere at one end while remaining submerged in the scented liquid at the other end.

Preferably, power provided by a wall outlet is used for the heating and lighting functions of the apparatus. Particularly, a resistor within the circuitry heats the aromatic, thereby causing the evaporation of the scented liquid into the atmosphere. The resistor is disposed in a heating block, such as a ceramic block. When power is provided to the resistor, the resistor heats the heating block, which in turn heats the aromatic. To further this process, the aromatic may be drawn up to the heating block via the capillary action of a wick. When power is provided to the resistor, light emitting diodes ("LEDs") within the circuitry illuminate. Preferably the bottle is clear or translucent, so as to enhance the nightlight functionality.

In the preferred embodiment, the LEDs also illuminate a decorative cover that partially surrounds the housing. Specifically, the decorative cover adds to the aesthetic effect of the invention, especially in conjunction with the LEDs. The cover may also evoke a particular mood or psychological effect. For example, in one embodiment, the cover is decorated in a holiday motif. Alternatively, the cover may take on a particular shape. For example, if a flower-scented aromatic is utilized, the decorative cover may be made in the shape of a flower to further add to the aesthetic effect of the device.

Further, in accordance with the present invention, the LEDs can also be used in conjunction with fiber optic cables. Fiber optic cables are thin strands of glass used to transmit light. When a light is applied to one end of a fiber optic cable, the whole cable is illuminated. In some embodiments of the present invention, the LEDs are used to illuminate fiber optic cables enhancing the nightlight functionality of the device and adding to the decorative effect of the device.

With respect to the circuitry of the present invention, multiple efficient designs are disclosed. In some embodiments, the AC input (from the wall outlet) is rectified into direct current ("DC"). The rectified current passes through a circuit which includes four LEDs and a resistor, all of which are wired in series. In an alternative embodiment, the AC input is not rectified. Rather, a shunt diode is wired in parallel to the LEDs (biased in the reverse direction) and in series with a resistor. In this configuration, the shunt diode allows for continuous current flow through the resistor. In this embodiment, current flows through the LEDs during half of the AC cycle and through the shunt diode during the other half of the AC cycle. Therefore, current flows through the resistor during both half-cycles of the full AC cycle. This allows the resistor to receive uninterrupted power from the wall outlet resulting in an efficient circuit. The LEDs only light during one half-cycle of the full AC cycle. However, the frequency with which the LEDs switch on and off is fast enough that the switching is not detected by the human eye.

Regardless of the circuit design, the resistor serves two functions. First, it provides heat to the aromatic. For example, the resistor, disposed in a heating block, may provide heat to a wick saturated with scented liquid which evaporates and is released into the atmosphere. The second function of the resistor is to regulate the current that passes through the LEDs. If too much current passes through the LEDs, the LEDs may malfunction or burn-out. If too little current passes through the LEDs they will not illuminate properly, thereby degrading the utility of the device. Thus, the resistor is a critical element of the present invention.

In alternative embodiments, more than one resistor may be used. For example, a plurality of resistors may be used to more evenly heat the aromatic. However, in such an embodiment, the resistors still serve two purposes (i.e., to heat the oil and to regulate the current that passes through the LEDs).

Thus, it is an object of the present invention to provide an electric air freshener.

It is also an object of the present invention to provide a nightlight.

Furthermore, it is an object of the present invention to provide a combined air freshener and nightlight.

Moreover, it is an object of the present invention to provide efficient circuitry that provides both heat and light.

Also, it is an object of the present invention to provide a heating resistor that receives current during both half-cycles of a full AC cycle.

It is yet another object of the present invention to light a bottle containing a scented liquid.

Further, it is an object of the present invention to light a decorative cover.

It is also an object of the present invention to heat a wick submerged in a scented liquid.

In addition, it is an object of the present invention to provide an aesthetically pleasing design.

These and other objects will become readily apparent to one skilled in the art upon review of the following description, figures, and claims.

SUMMARY OF THE DRAWINGS

A further understanding of the present invention can be obtained by reference to a preferred embodiment, along with some alternative embodiments, set forth in the illustrations of the accompanying drawings. Although the illustrated embodiments are merely exemplary of systems for carrying out the present invention, the organization and method of operation of the invention in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings.

DETAILED DESCRIPTION OF THE PREFERRED EMBODIMENTS

As required, detailed illustrative embodiments of the present invention are disclosed herein. However, techniques, systems and operating structures in accordance with the present invention may be embodied in a wide variety of forms and modes, some of which may be quite different from those in the disclosed embodiments. Consequently, the specific structural and functional details disclosed herein are merely representative, yet in that regard, they are deemed to afford the best embodiments for purposes of disclosure and to provide a basis for the claims herein which define the scope of the present invention. The following presents a detailed description of a preferred embodiment (as well as some alternative embodiments) of the present invention.

As discussed above, the present invention is a combined air freshener/nightlight apparatus, wherein the components designated for the nightlight operate symbiotically with the components designated for the air freshener. The result is a unique and novel design which excels in both arts. Initially, to create the apparatus of the present invention, an appropriate housing may be utilized for containing all of the necessary circuitry and for providing structural support.

Figure 1:
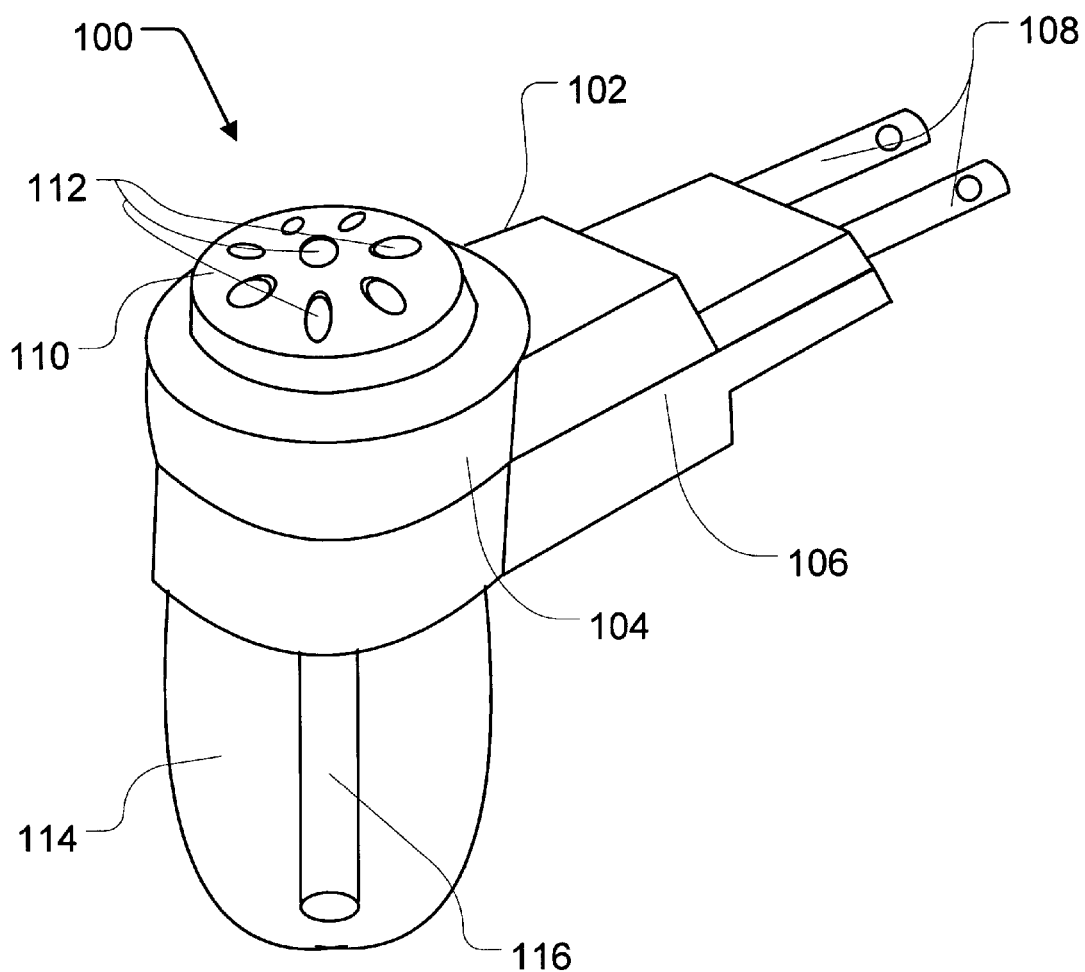
FIG. 1 is a perspective view showing the housing of the device and a container which holds the aromatic in accordance with the one embodiment of the present invention.

A perspective view of such a housing is depicted as housing 102 of air freshener 100 in FIG. 1. Housing 102 comprises cylindrical portion 104 and plug portion 106. Male electrical connectors 108 protrude from inside housing 102 for plugging into an AC outlet. The upper portion of housing 102 comprises dome 110 which includes vents 112. Vents 112 help dissipate the scented liquid. Specifically, vents 112 allow an upward convection current to flow through housing 102, which efficiently dissipates the volatized scented oil. Further, vents 112 also allow light emitted by the LEDs to escape from housing 102. A container such as bottle 114 contains an aromatic, such as a scented liquid, which is to be vaporized by air freshener 100 and can be screwed into housing 102. The screw connection between bottle 114 and housing 102 may be reverse-threaded to prevent other improper bottles from being used with air freshener 100. Wick 116 extends vertically from the bottom of bottle 114 and protrudes from the top of bottle 114 (not shown in FIG. 1). A pin (not pictured) may be inserted through wick 116 to secure wick 116 in place. This prevents the removal of wick 116 from bottle 114 so that the contents of bottle 114 are not spilled or tampered with.

Figure 2:
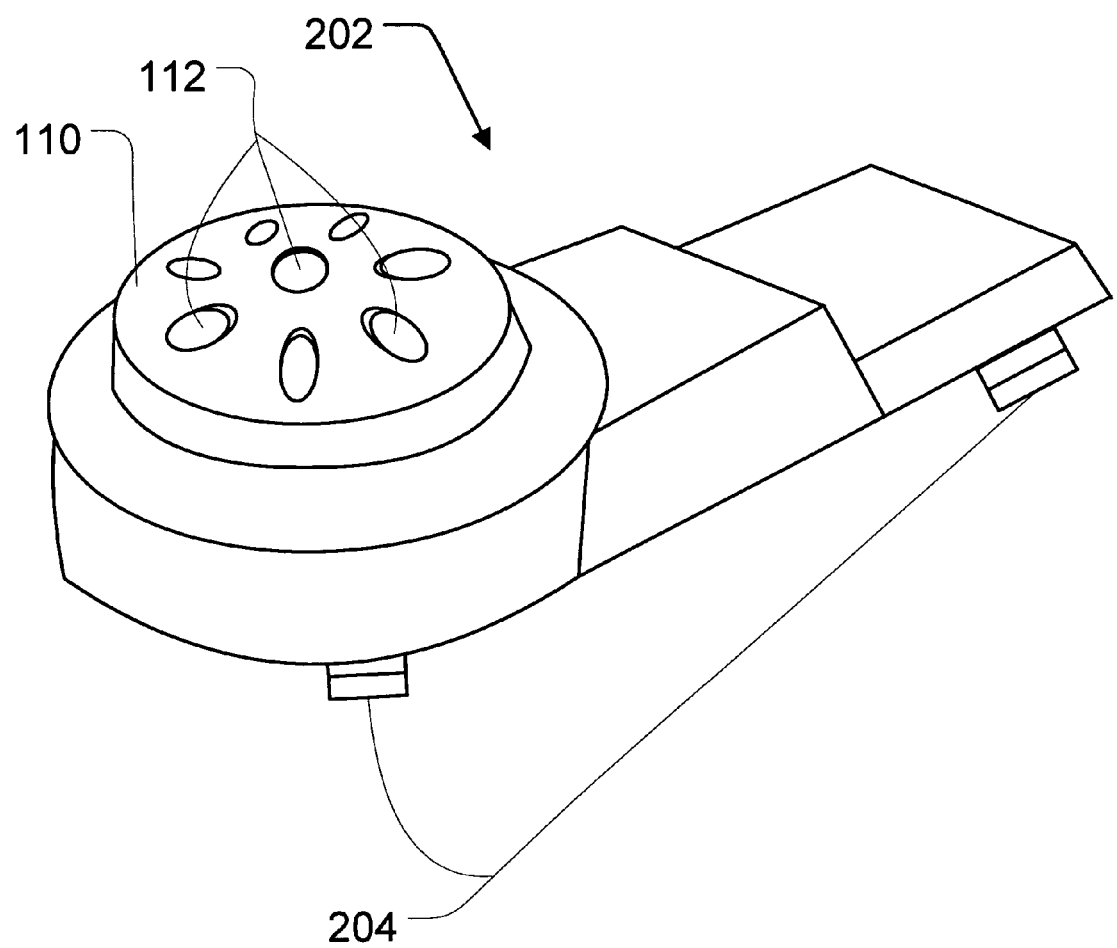
FIG. 2 is a perspective view showing the top portion of the housing in accordance with the one embodiment of the present invention.

In one embodiment, the housing encloses the circuitry of the apparatus. For example, the housing can be comprised of two separate pieces which are snapped or glued together to hold the circuitry and to provide structural support. FIG. 2 is a perspective view of the top piece of such a housing. Top piece 202 includes dome 110 and vents 112. Also included are snaps 204 which enable top piece 202 to be attached to the bottom half of the housing. Thus, top piece 202 contains the structure to allow the dispersion of fragrance and light into the atmosphere. Top piece 202 also provides structural support (not pictured) for male electrical connectors 108 which plug into a standard wall outlet.

Figure 3:
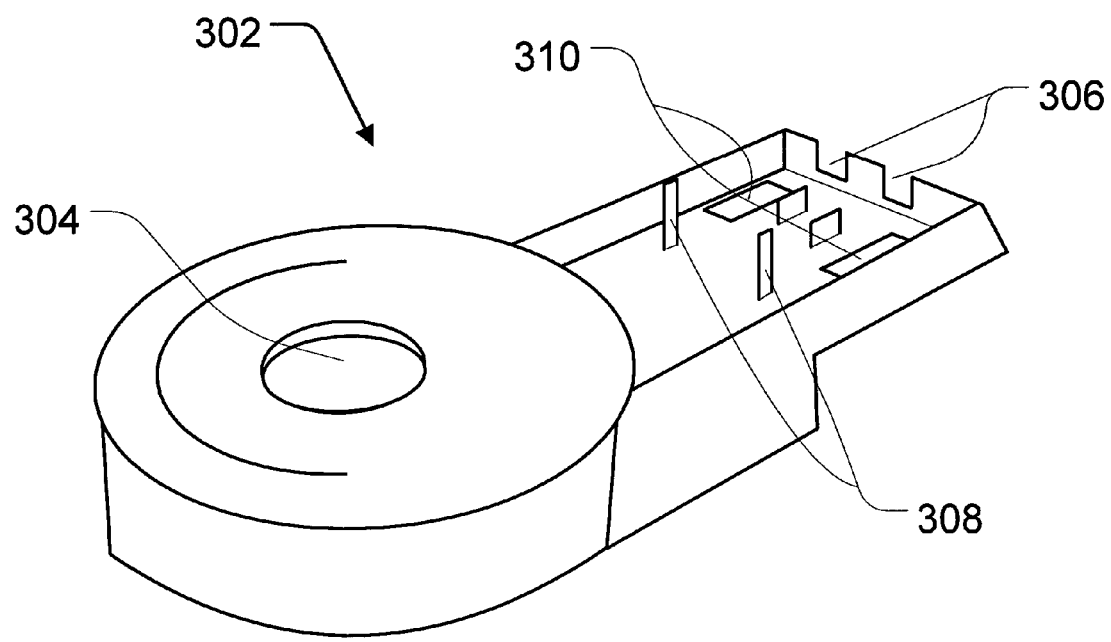
FIG. 3 is a perspective view showing the bottom portion of the housing in accordance with one embodiment of the present invention.

FIG. 3 is a perspective view of the bottom half of the housing. Bottom piece 302 holds the circuitry of the present invention. Bottom piece 302 also provides structure for holding the bottle and wick. Specifically, bottom piece 302 includes a screw connection (not pictured) and wick hole 304. Wick 116 protrudes through wick hole 304 so as to be heated by the circuitry of the present invention. Bottle 114 screws into the screw connection of bottom piece 302. Bottom piece 302 also contains structure, openings 306, to allow male electrical connectors 108 to protrude from the housing. Bottom piece 302 also contains structure, supports 308, to hold the circuitry of the present invention. Finally, to connect to top piece 202, bottom piece 302 also includes snap holes 310 which receive snaps 204.

Figure 4:
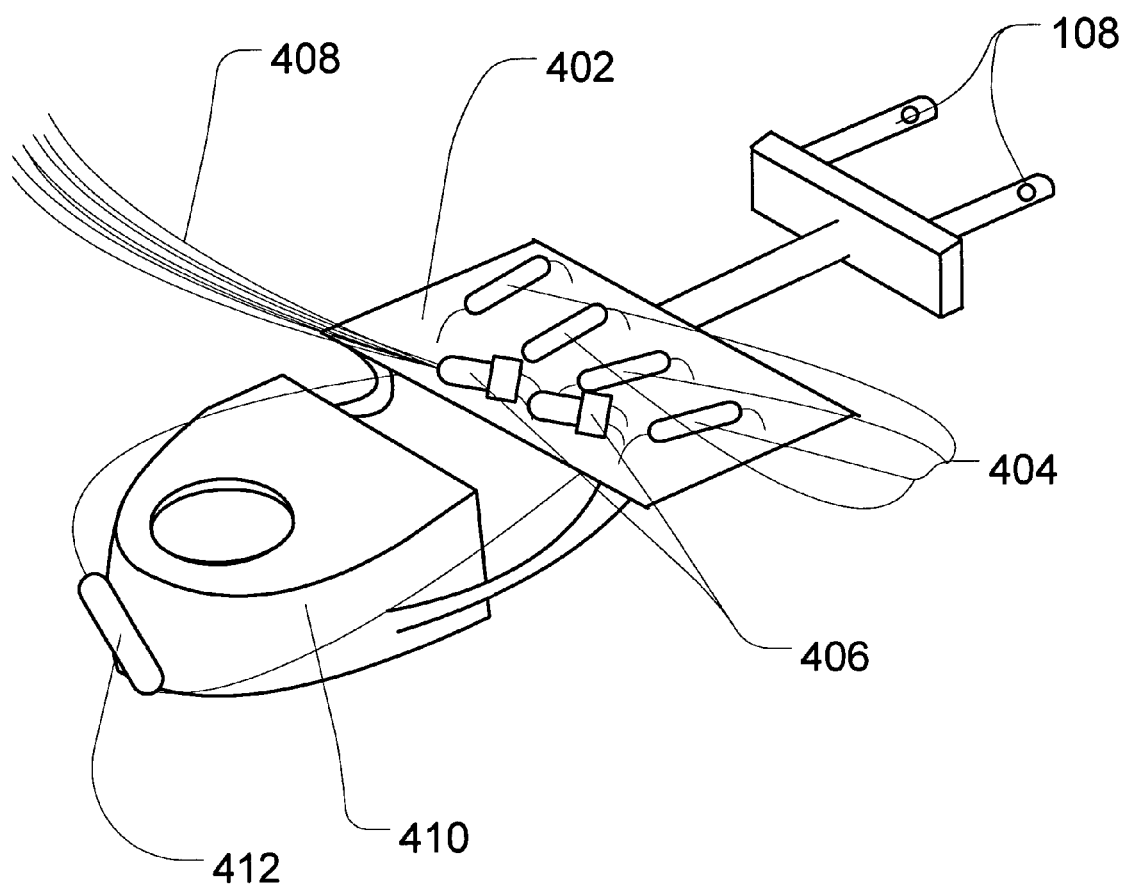
FIG. 4 is a perspective view showing the circuitry in accordance with one embodiment of the present invention.

FIG. 4 is a perspective view of one embodiment of the circuitry. As is depicted, the circuitry of the present invention connects to male connectors 108. Specifically, in the example depicted in FIG. 4, circuit board 402 connects four diodes 404 to male connectors 108 and four light emitting diodes, LEDs 406 (only two LEDs 406 are pictured). One or more of LEDs 406 can be connected to fiber optic cables 408. For example, as depicted in FIG. 4, one LED 406 is connected to fiber optic cables 408. Further, a resistor (not pictured, but shown later as resistor 706), contained within a heating block such as ceramic block 410 is also connected to circuit board 402, as is thermal fuse 412. The circuitry is preferably enclosed by housing 102.

Regardless of the specific design, the circuitry operates to provide power to the resistor. For example, in the embodiment depicted in FIG. 4, the resistor heats ceramic block 410, which in turn holds and heats wick 116. Specifically, ceramic block 410 contains a hole, ceramic hole 414. The end of wick 116 that protrudes from bottle 114 fits within ceramic hole 414.

When the resistor is powered by the circuitry, the resistor emits heat. Some of this heat is transferred to ceramic block 410, and in turn, to wick 116. Scented liquid contained within bottle 114 diffuses into the protruding end of wick 116 via capillary action. This scented liquid is heated by the resistor (through ceramic block 410) and dispersed into the surrounding environment. In this manner, the device emits an aroma.

In addition to heating wick 116, the resistor regulates the current that passes through LEDs 406. LEDs illuminate when current passes through them. The strength of the illumination positively relates to the amount of current. However, too much current can cause the LEDs to malfunction, break-down or burn-out. Thus, a resistor is necessary to regulate the current that passes through LEDs 406. The present invention optimally uses one resistor to regulate the current through LEDs 406 and to properly heat wick 116.

The resistor must be composed of materials that predictably inhibit the flow of current. For example, the resistor may comprise a non-conducting rod coated with tin-oxide. Alternatively, the resistor may be coated with nickel-chromium.

The purpose of thermal fuse 412 is to open the circuit before the melting point of the housing is reached. Specifically, as is well known in the art, thermal fuse 412 breaks down and acts as an open circuit if the temperature exceeds a predetermined threshold. For example, in one embodiment, thermal fuse 412 has a threshold temperature of 325 degrees Fahrenheit. Alternatively, in place of thermal fuse 412, an electrical fuse may be used which is designed to prevent an overload of current from passing through the circuitry of the present invention.

The embodiment of the circuitry depicted in FIG. 4 utilizes circuit board 402, though the components of the circuitry can be wired together without a circuit board (i.e., with point-to-point connections). Further, this embodiment uses one resistor and four LEDs 406, however any number of resistors or LEDs 406 may be used in the circuitry of the present invention. Specifics of exemplary circuit designs are depicted in FIGS. 7-10 and are discussed further infra.

Figure 5:
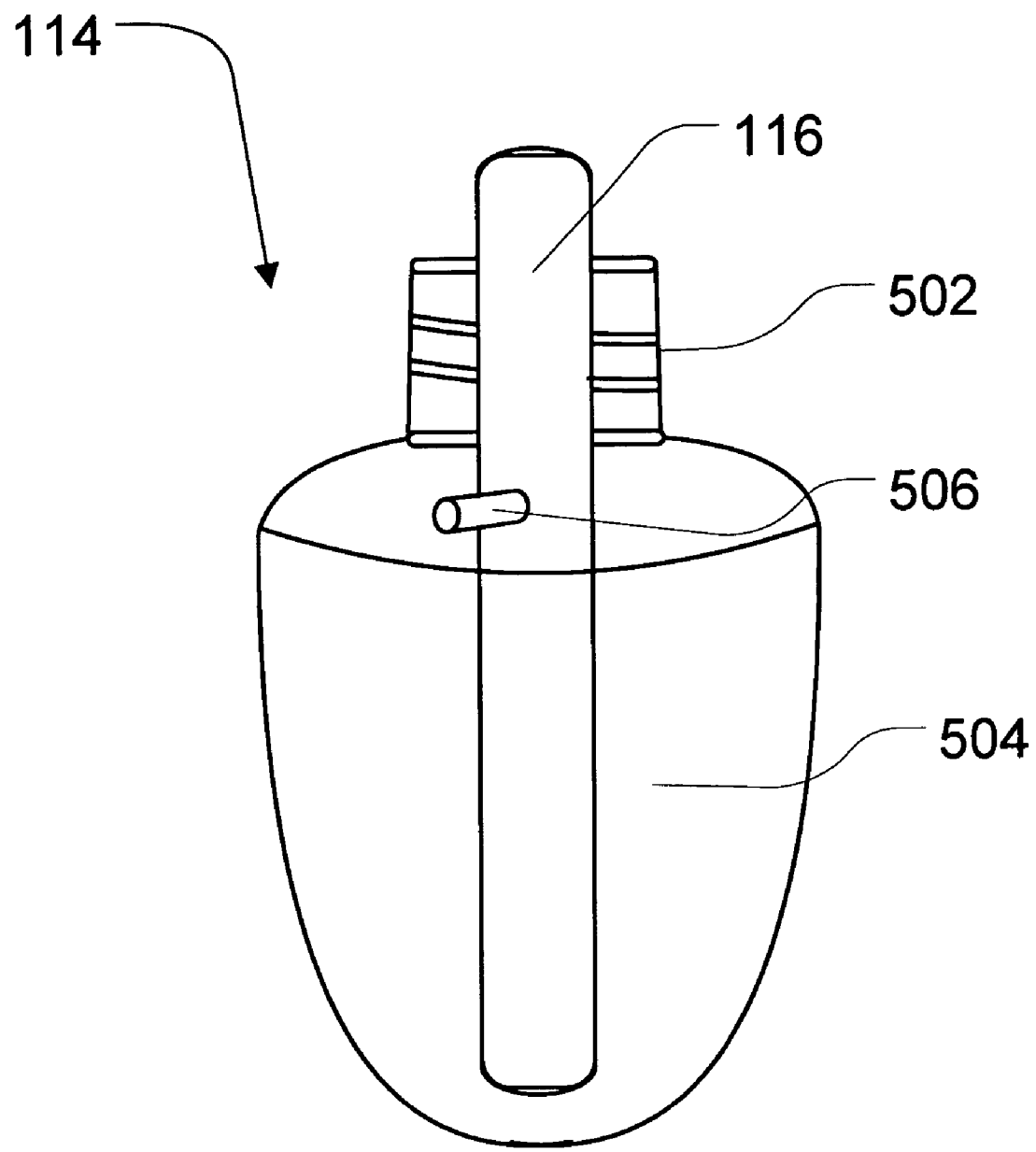
FIG. 5 is a side view showing a bottle which holds an aromatic and showing a wick which is partially submerged in the scented liquid in accordance with one embodiment of the present invention.

A closer, more detailed view of bottle 114 is illustrated in FIG. 5. Here, wick 116 can be seen protruding from neck 502 of container 504. The other end of wick 116 is submerged in scented liquid held by bottle 114. Wick 116 absorbs the scented liquid through capillary action and allows the scented liquid to evaporate into the surroundings at the distal end of wick 116. Pin 506 prevents wick 116 from being pulled out from bottle 114. As shown, neck 502 is threaded to facilitate the coupling of bottle 114 to housing 102. Preferably, neck 502 is reverse-threaded. However, the present invention functions equally effectively with standard threading. Also, container 504 is preferably clear or translucent. As discussed in greater detail infra, container 504 is clear or translucent so as to be illuminated by LEDs 406.

Figure 6:
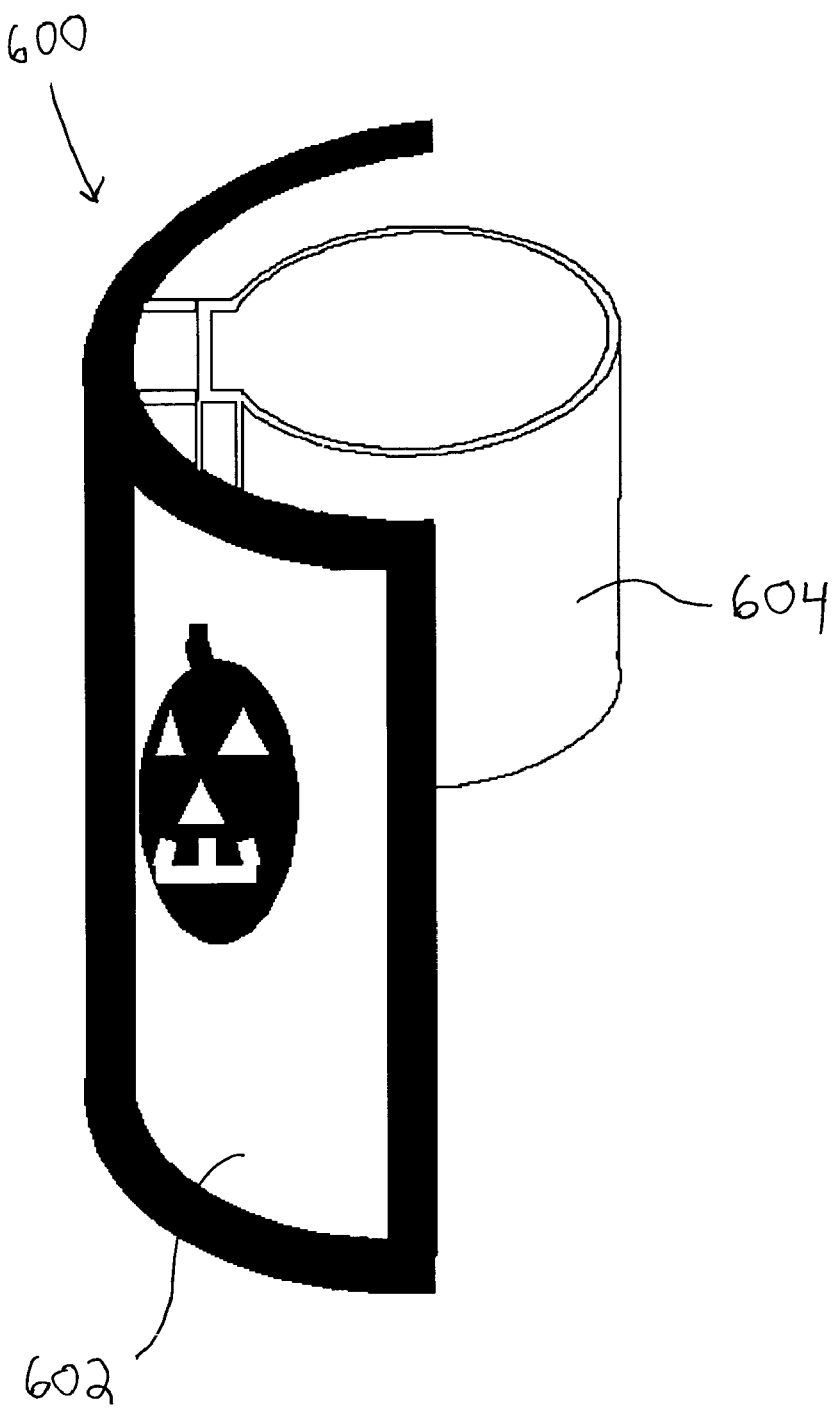
FIG. 6 depicts a decorative cover that is illuminated by the LEDs in accordance with one embodiment of the present invention.

To improve the aesthetic qualities of the present invention, various portions of air freshener 100 may be decorated. For example, FIG. 6 is a perspective view of decorative cover 600. Decorative cover 600 includes decorative shield 602 and cylinder 604. Cylinder 604 may be attached or glued to housing 102. Specifically, cylinder 604 may attach around dome 110 of housing 102. Decorative shield 602 is preferably clear or translucent so as to allow the LEDs to emit light through the shield. Further decorative shield 602 may include a decorative design to further the aesthetic qualities of the present invention. For example, decorative shield 602 includes a holiday motif. Of course decorative cover 600 and decorative shield 602 may take on various shapes and designs as desired. As another example, if the aromatic is flower-scented, the decorative shield can be flower-shaped to further the aesthetic effect of air freshener 100. Alternatively the decorative shield may depict flowers where the depiction is illuminated by LEDs 406.

FIGS. 7-10 are electric schematics of the circuitry of the present invention. Each schematic illustrates an alternative embodiment of the present invention. However, such embodiments are merely exemplary and are not meant to limit the present invention.

Figure 7:
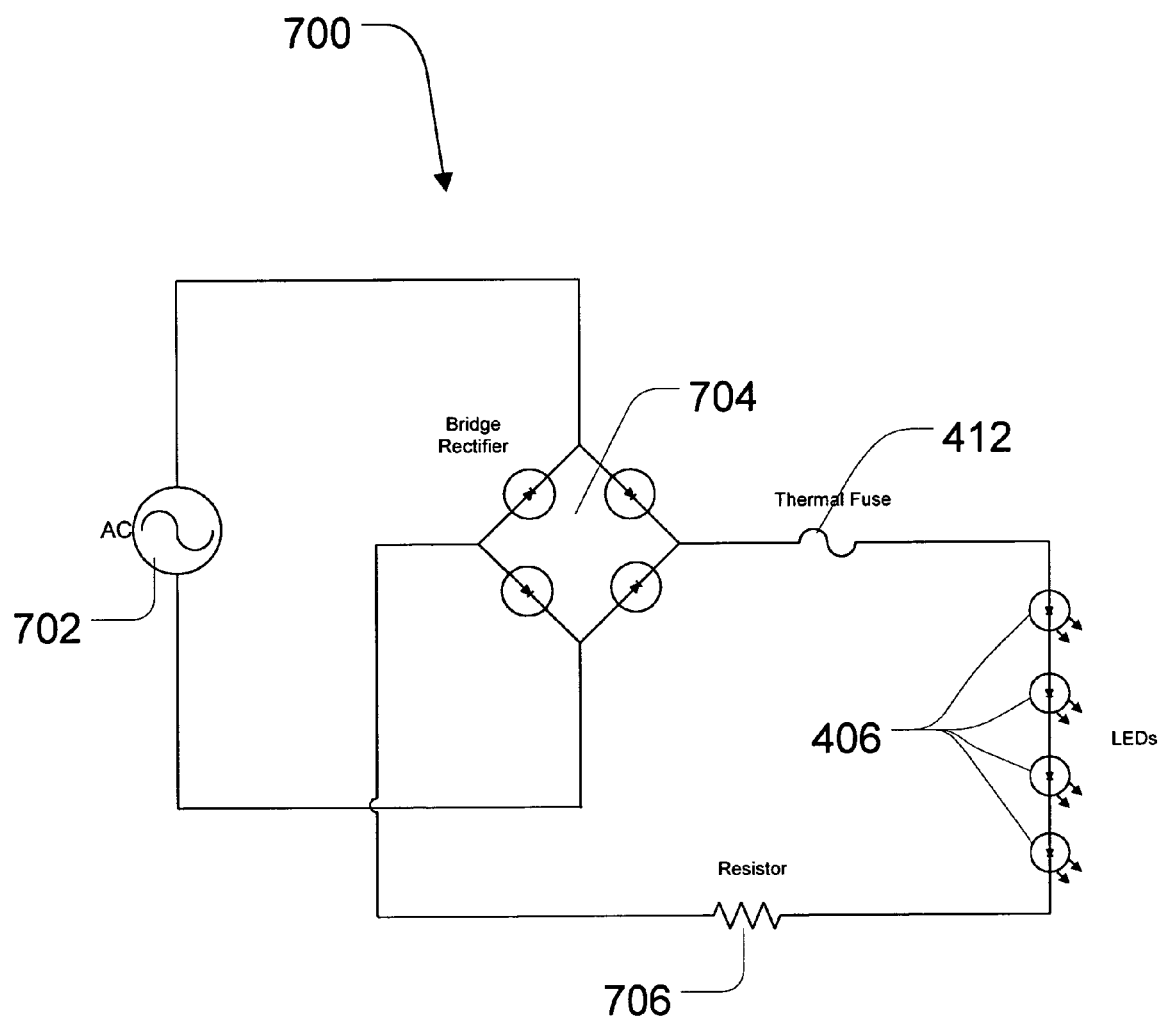
FIG. 7 is an electrical schematic of the circuit according to one embodiment of the present invention.

FIG. 7 is a schematic circuit diagram more specifically illustrating one of the circuit designs. As shown, circuit 700 is designed to receive power from AC source 702. The alternating current from AC source 702 is rectified with full-wave bridge rectifier 704. Full-wave bridge rectifier 704 is comprised of four diodes 404. Full-wave bridge rectifier 704 is designed to convert the alternating current to direct current ("DC"). The resulting direct current passes through thermal fuse 412, four LEDs 406, and resistor 706 and back to bridge rectifier 704 to complete the circuit. Resistor 706 is preferably disposed in ceramic block 410.

Resistor 706 preferably has a resistance of approximately 7500 ohms. Such a resistance optimally heats the aromatic while providing optimal current to LEDs 406. Resistor 706 may comprise various materials such as tin-oxide or nickel-chromium. The material with which resistor 706 is comprised does not substantially change the present invention so long as resistor 706 is small enough to be disposed in ceramic block 410 and so long as resistor 706 has the necessary resistance to optimally heat the aromatic while providing optimal current to LEDs 406.

Full-wave bridge rectifier 704 ensures that LEDs 406 and resistor 706 are powered during the full AC cycle. Resistor 706 provides the four LEDs 406 with optimal current such that the LEDs are illuminated but do not break down. Further, resistor 706 produces enough heat to heat wick 116 which holds the scented liquid motivating its release into the atmosphere. Therefore, circuit 700 is optimally designed for air freshener and nightlight functionality.

Figure 8:
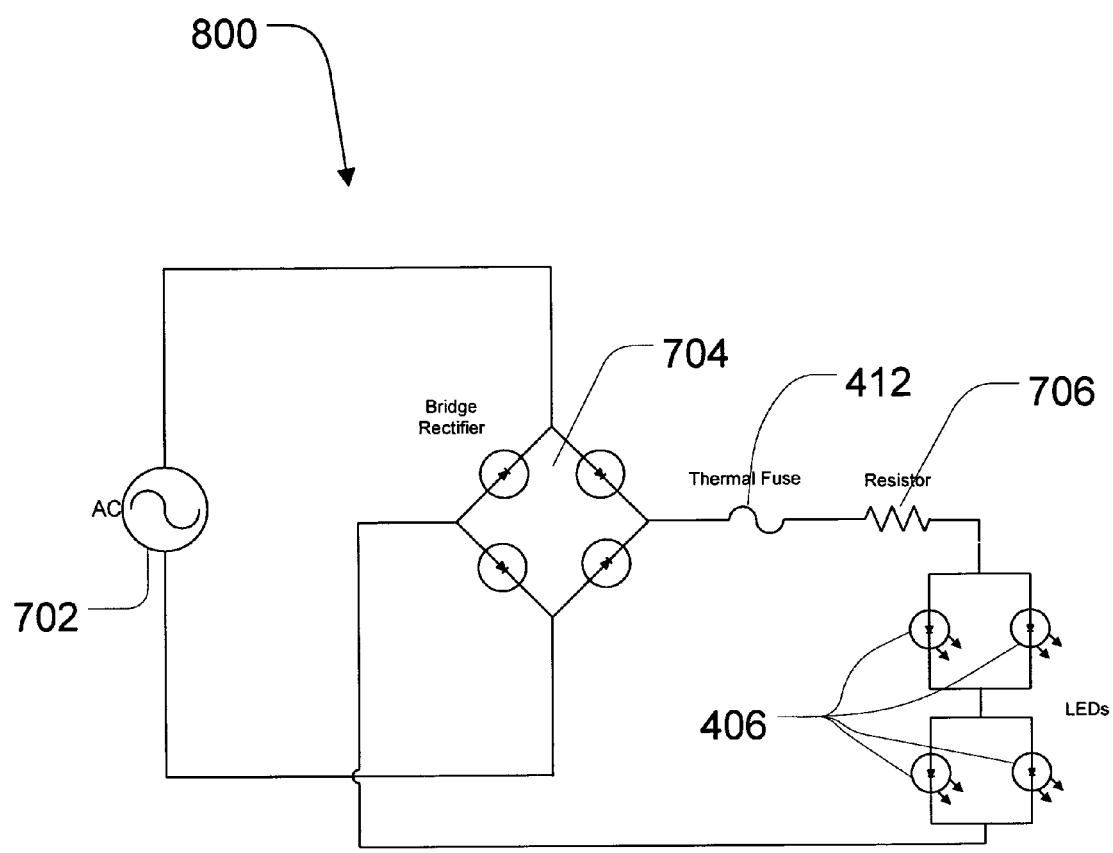
FIG. 8 is an electrical schematic of an alternative circuit according to an alternative embodiment of the present invention.

FIG. 8 is an electrical schematic of an alternative circuit, circuit 800, according to the present invention. Again, circuit 800 is designed to receive alternating current (AC) from AC source 702. Also, as in the previous design (see FIG. 7), full-wave bridge rectifier 704 converts the alternating current to direct current. The resulting direct current passes through thermal fuse 412, resistor 706 and four LEDs 406. In circuit 800, the four LEDs 406 are arranged as two sets of parallel LED pairs connected in series.

Figure 9:
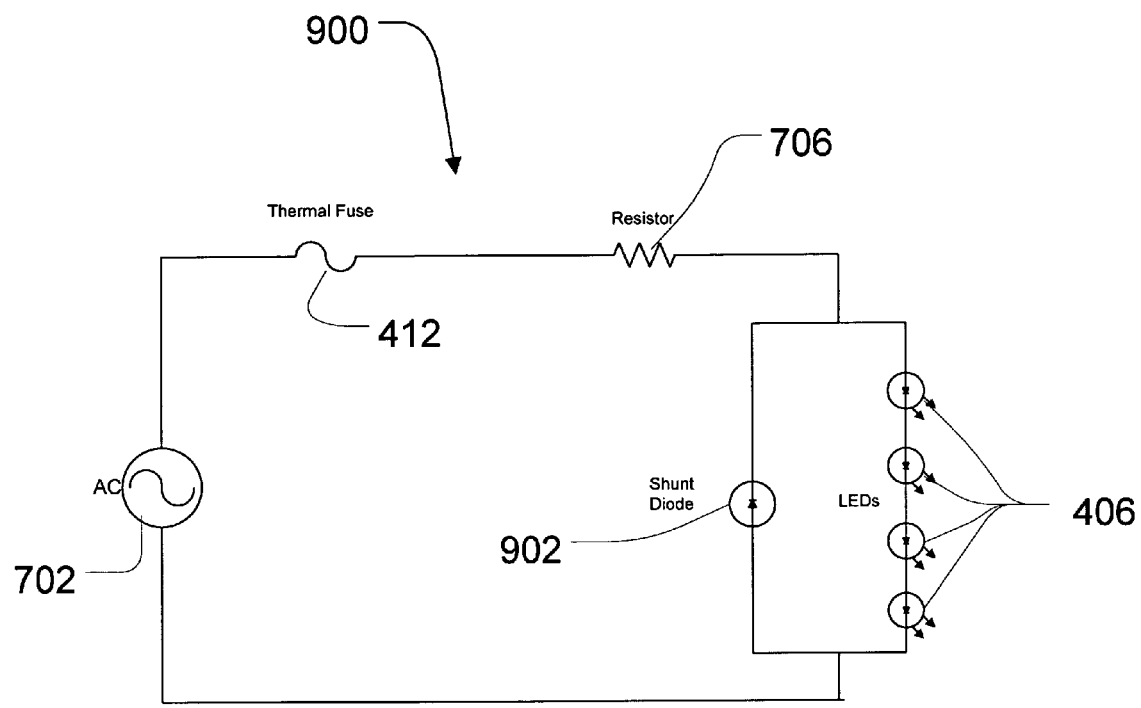
FIG. 9 is an electrical schematic of another alternative circuit according to another alternative embodiment of the present invention.

Unlike the previous two designs, the circuit design depicted in FIG. 9 does not utilize full-wave bridge rectifier 704. Instead, circuit 900 utilizes shunt diode 902. Like circuit 700, circuit 900 contains four LEDs 406 connected in series with each other, and also utilizes resistor 706 and thermal fuse 412. However, circuit 900 contains shunt diode 902 wired in parallel to the LEDs (biased in the reverse direction) and in series with resistor 706. In this configuration, shunt diode 902 allows for continuous current flow through resistor 706. Specifically, current flows through LEDs 406 during half of the AC cycle and through shunt diode 902 during the other half of the AC cycle. Current flows through resistor 706 during both half-cycles of the full AC cycle. This allows resistor 706 to receive uninterrupted power from AC source 702 resulting in an efficient circuit. LEDs 406 only light during one half-cycle of the full AC cycle. However, the frequency with which LEDs 406 switch on and off is fast enough that the switching is not detected by the human eye. Therefore, it is perceived that LEDs 406 are always emitting light.

Figure 10:
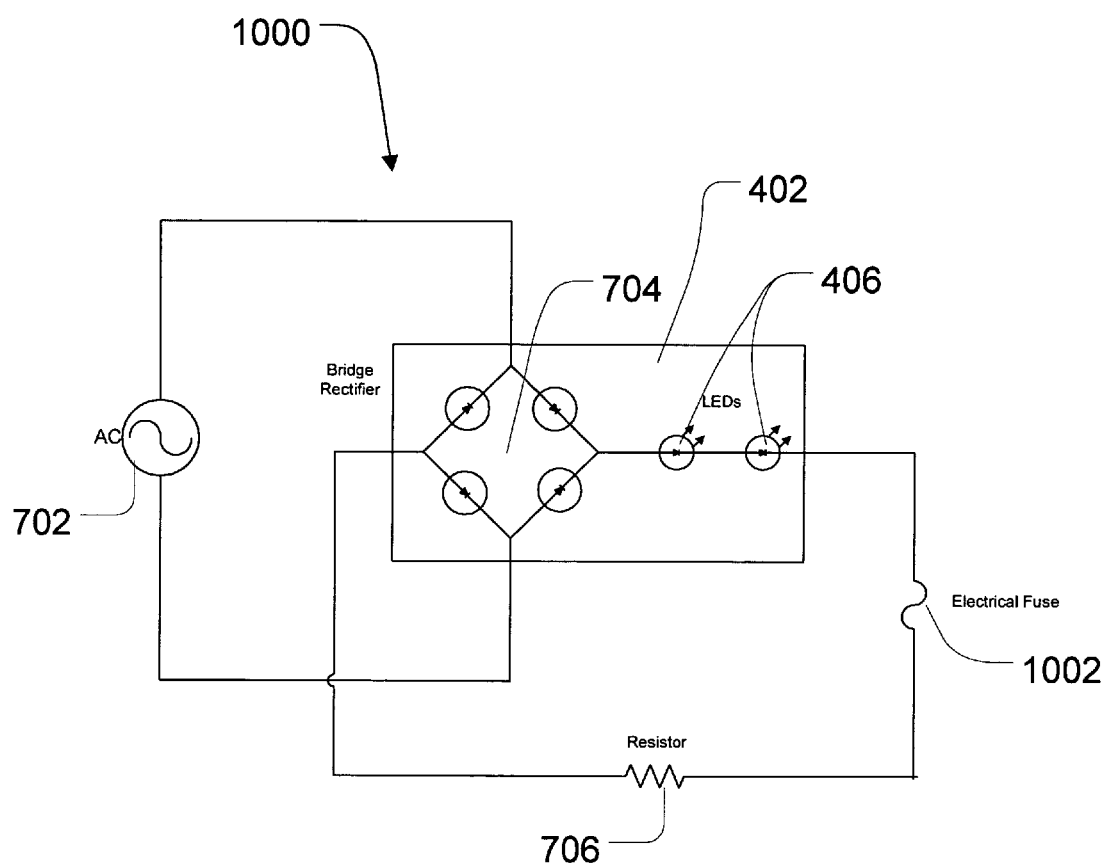
FIG. 10 is an electrical schematic of yet another alternative circuit according to yet another alternative embodiment of the present invention.

In yet another circuit design, depicted in FIG. 10, a two-layer printed circuit board, circuit board 402, is utilized as part of circuit 1000. The design in FIG. 10 incorporates full-wave bridge rectifier 704, but unlike the previous examples, circuit 1000 employs only two LEDs 406. Further, circuit 1000 utilizes electrical fuse 1002 in place of thermal fuse 412. Electrical fuse 1002 is designed to prevent an overload of current from passing through the circuit.

One LED 406 is located slightly above the heater block, and one LED 406 is located slightly below the heater block. The illuminating effects of LEDs 406, however, remain the same. The overall circuit design of circuit 1000 is similar to that of circuit 700 (see FIG. 7). The differences include: 1) the positions of thermal fuse 412, LEDs 406, and resistor 706 relative to each other within the circuit; 2) the number of LEDs 406; 3) the use of electrical fuse 1002 in place of thermal fuse 412; and 4) the use of circuit board 402 to connect a portion of the circuitry. Specifically, all of the connections of full-wave bridge rectifier 704 and the connections between LEDs 406 are made via circuit board 402.

While the present invention has been described with reference to one or more preferred embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention.

We claim:

1. An air freshener comprising:
   a circuit having a plurality of light emitting diodes and at least one resistor wherein said at least one resistor is disposed in a heating block;
   electrical connectors coupled to said circuit to receive current from a power source and to provide said current to said circuit;
   a container for holding a substance to be heated;
   a housing which contains said circuit further comprising a socket for attaching said container;
   a semi-cylindrically shaped decorative cover attached to said housing which partially surrounds said housing and at least a portion of said container such that a gap is formed between said decorative cover, said container and said housing;
   wherein said housing and said container are at least partially located within the circumference of said semi-cylinder;
   wherein said decorative cover is incapable of dissipating fragnance;
   wherein said decorative cover is illuminated by said plurality of light emitting diodes; and
   wherein said at least one resistor heats said heating block so as to heat said substance held by said container thereby accelerating the emission of an aroma associated with said substance and wherein said at least one resistor also limits said current provided to said plurality of light emitting diodes.

2. The device in accordance with claim 1 wherein said power source provides alternating current and wherein said circuit further comprises a rectifier.

3. The device in accordance with claim 1 wherein said power source provides alternating current and wherein said circuit further comprises a shunt diode connected in parallel with said plurality of light emitting diodes and in series with said at least one resistor.

4. The device in accordance with claim 1 wherein said heating block is comprised of a ceramic material.

5. The device in accordance with claim 1 further comprising:
at least one fiber optic cable wherein said at least one fiber optic cable is coupled to said plurality of light emitting diodes.

6. The device in accordance with claim 1 wherein said circuit further includes a thermal fuse.

7. The device in accordance with claim 1 wherein said circuit further includes an electrical fuse.

8. The device in accordance with claim 1 wherein said container is translucent.

9. The device in accordance with claim 8 wherein said container is illuminated by said plurality of light emitting diodes.

10. The device in accordance with claim 1 further comprising:
a wick inserted into said container wherein one end of said wick protrudes from said container.

11. The device in accordance with claim 10 wherein said one end of said wick that protrudes from said container is held by said heating block.

12. The device in accordance with claim 1 wherein said housing further includes at least one dome and at least one vent to facilitate release of said aroma and to facilitate emission of light generated by said plurality of light emitting diodes.

13. A method for efficiently combining nightlight and air freshener capabilities in a single decorative device comprising the steps of:
receiving current from a power source;
providing said current to a circuit including a resistor and a plurality of light emitting diodes wherein said resistor limits said current provided to said plurality of light emitting diodes and wherein said resistor further heats a heating block; and
illuminating a decorative device comprising:
a container for holding an aromatic to be heated;
a housing which contains said circuit further comprising a socket for attaching said container;
a semi-cylindrically shaped decorative cover attached to said housing which partially surrounds said housing and at least a portion of said container such that a gap is formed between said decorative cover, said container and said housing;
wherein said housing and said container are at least partially located within the circumference of said semi-cylinder;
wherein said decorative cover is incapable of dissipating fragnance
wherein said decorative cover is illuminated by said plurality of light emitting diodes; and
wherein said heating block heats said aromatic to motivate the release of an aroma.

14. A method according to claim 13 wherein said current is alternating current and said circuit further includes a rectifier.

15. A method according to claim 13 wherein said current is alternating current and said circuit further includes a shunt diode connected in parallel with said plurality of light emitting diodes and in series with said resistor.

16. A method according to claim 13 wherein said heating block is a ceramic block.

17. A method according to claim 13 further comprising the step of:
illuminating at least one fiber optic cable by coupling said at least one fiber optic cable to said plurality of light emitting diodes.

18. A method according to claim 13 wherein said heating block heats said aromatic using conduction.

19. A method according to claim 13 wherein said heating block heats said aromatic using convection.

20. A method according to claim 13 wherein said heating block heats said aromatic using radiation.

21. A method according to claim 13 wherein said decorative cover depicts at least one flower.

22. A method according to claim 13 wherein said decorative cover is a flower-like structure.

23. A method according to claim 13 wherein said aromatic is comprised of a hydrocarbon.

24. A method according to claim 23 wherein said hydrocarbon is a scented liquid.

25. A method according to claim 24 further comprising the step of:
holding said scented liquid in a container.

26. A method according to claim 25 wherein said container is translucent.

27. A method according to claim 25 wherein said container also comprises a wick wherein one end of said wick protrudes from said container.

28. A method according to claim 27 wherein said one end of said wick that protrudes from said container is held by said heating block.

29. An air freshener comprising:
a circuit having a plurality of light emitting diodes, at least one resistor disposed in a heating block and a rectifier;
electrical connectors coupled to said circuit to receive alternating current from a power source and to provide said alternating current to said rectifier wherein said rectifier provides rectified alternating current to said plurality of light emitting diodes and to said at least one resistor;
a container for holding a scented oil to be heated;
a wick inserted into said container wherein one end of said wick protrudes from said container;
a housing for holding said circuit wherein said housing also comprises a socket for holding said container and said wick; and
a semi-cylindrically shaped decorative cover attached to said housing which partially surrounds said housing and at least a portion of said container such that a gap is formed between said decorative cover, said container and said housing;
wherein said housing and said container are at least partially located within the circumference of said semi-cylinder;
wherein said decorative cover is incapable of dissipating fragrance;
wherein said decorative cover is illuminated by said plurality of light emitting diodes; and
wherein said at least one resistor heats said heating block and said wick so as to heat said scented oil held by said container thereby accelerating the emission of an aroma and wherein said at least one resistor also limits said rectified alternating current provided to said plurality of light emitting diodes wherein said plurality of light emitting diodes illuminates.

30. The device in accordance with claim 29 wherein said heating block comprises a ceramic material.

31. The device in accordance with claim 29 further comprising:
at least one fiber optic cable wherein said at least one fiber optic cable is coupled to said plurality of light emitting diodes.

32. The device in accordance with claim 29 wherein said circuit further includes a thermal fuse.

33. The device in accordance with claim 29 wherein said circuit further includes an electrical fuse.

34. The device in accordance with claim 29 wherein said housing further includes at least one dome and at least one vent to facilitate release of said aroma and to facilitate emission of light generated by said plurality of light emitting diodes.

35. The device in accordance with claim 29 wherein said container further comprises a threaded neck and said socket of said housing is threaded so that said container can be screwed into said housing.

36. The device in accordance with claim 29 wherein said container further comprises a reverse threaded neck and said socket of said housing is reverse threaded so that said container can be screwed into said housing.

37. The device in accordance with claim 29 wherein said container is translucent.

38. The device in accordance with claim 37 wherein said container is illuminated by said plurality of light emitting diodes.

39. The device in accordance with claim 29 wherein said rectifier is a full-wave bridge rectifier.

40. The device in accordance with claim 39 wherein said full-wave bridge rectifier includes four diodes.

41. The device in accordance with claim 29 wherein said decorative cover is flower-shaped.

42. The device in accordance with claim 29 wherein said decorative cover depicts at least one flower.

43. An air freshener comprising:
   a circuit having a plurality of light emitting diodes, at least one resistor disposed in a heating block and a shunt diode wherein said shunt diode is connected in parallel with said plurality of light emitting diodes and in series with said at least one resistor;
   electrical connectors coupled to said circuit to receive alternating current from a power source and to provide said alternating current to said circuit;
   a container for holding a scented oil to be heated;
   a wick inserted into said container wherein one end of said wick protrudes from said container;
   a housing for holding said circuit wherein said housing also comprises a socket for holding said container and said wick; and
   a semi-cylindrically shaped decorative cover attached to said housing which partially surrounds said housing and at least a portion of said container such that a gap is formed between said decorative cover, said container and said housing;
   wherein said housing and said container are at least partially located within the circumference of said semi-cylinder;
   wherein said decorative cover is incapable of dissipating fragrance
   wherein said decorative cover is illuminated by said plurality of light emitting diodes; and
   wherein said at least one resistor heats said heating block and said wick so as to heat said scented oil held by said container thereby accelerating the emission of an aroma and wherein said at least one resistor also limits said alternating current provided to said plurality of light emitting diodes such that said plurality of light emitting diodes illuminates.

44. The device in accordance with claim 43 wherein said heating block comprises a ceramic material.

45. The device in accordance with claim 43 further comprising:
   at least one fiber optic cable wherein said at least one fiber optic cable is coupled to said plurality of light emitting diodes.

46. The device in accordance with claim 43 wherein said circuit further includes a thermal fuse.

47. The device in accordance with claim 43 wherein said circuit further includes an electrical fuse.

48. The device in accordance with claim 43 wherein said housing further includes at least one dome and at least one vent to facilitate release of said aroma and to facilitate emission of light generated by said plurality of light emitting diodes.

49. The device in accordance with claim 43 wherein said container further comprises threaded neck and said socket of said housing is threaded so that said container can be screwed into said housing.

50. The device in accordance with claim 43 wherein said container further comprises a reverse threaded neck and said socket of said housing is reverse threaded so that said container can be screwed into said housing.

51. The device in accordance with claim 43 wherein said container is translucent.

52. The device in accordance with claim 51 wherein said container is illuminated by said plurality of light emitting diodes.

53. The device in accordance with claim 43 wherein said decorative cover is flower shaped.

54. The device in accordance with claim 43 wherein said decorative cover depicts at least one flower.

* * * * *